United States Patent [19]
Paul

[11] Patent Number: 6,005,028
[45] Date of Patent: Dec. 21, 1999

[54] ORGANIC-INORGANIC HYBRID COMPOSITES FOR DENTAL RESTORATIVE MATERIAL

[75] Inventor: Partha P. Paul, San Antonio, Tex.

[73] Assignee: Southwest Research Institute, San Antonio, Tex.

[21] Appl. No.: 08/694,419

[22] Filed: Aug. 12, 1996

[51] Int. Cl.$^6$ .............................. C08F 30/04; A61K 6/093
[52] U.S. Cl. .................. 523/216; 523/116; 523/212; 523/213; 524/397; 524/413; 524/443; 524/859; 522/172; 525/326.5; 526/279
[58] Field of Search .................... 524/859, 413, 524/443, 397; 523/116, 212, 213, 216; 522/172; 526/279; 525/326.5

[56] References Cited

U.S. PATENT DOCUMENTS

| | | | |
|---|---|---|---|
| 4,011,253 | 3/1977 | Blount | 528/32 |
| 4,256,873 | 3/1981 | Blount | 528/421 |
| 4,381,918 | 5/1983 | Ehrnford | 433/199 |
| 5,064,877 | 11/1991 | Nass et al. | 522/172 |
| 5,132,337 | 7/1992 | Panster et al. | 523/117 |
| 5,231,156 | 7/1993 | Lin | 526/279 |
| 5,426,134 | 6/1995 | Rheinberger et al. | 523/118 |

OTHER PUBLICATIONS

Goodwin et al., *Inorg. Chem*, 29:1216–1220 (1990).
Abe et al., *J. Polymer Science*, 21:41–53 (1983).
Iler et al., *Industrial and Engineering Chemistry*, 39 (11):1379–1384 (1947).
Ellsworth et al., *Chem. Mater.*, 5:839–844 (1993).

*Primary Examiner*—Andrew B. C. Merriam
*Attorney, Agent, or Firm*—John L. Sigalos

[57] ABSTRACT

Alkoxides with polymerizable groups are single source precursors for organic-inorganic hybrid composites possessing good mechanical properties. Additional function groups of the alkoxides provide enhanced adhesion to other surfaces, such as dentin. The selection of specific organic monomers having functional groups that are responsible for enhanced properties of the organic-inorganic hybrid composites is important. Single source precursors containing the desired functional groups are condensed and polymerized into the organic-inorganic hybrid composites with enhanced properties which are particularly useful as dental composites.

29 Claims, No Drawings

ORGANIC-INORGANIC HYBRID COMPOSITES FOR DENTAL RESTORATIVE MATERIAL

BACKGROUND OF THE INVENTION

1. Field of the Invention

The present invention relates generally to the field of organic-inorganic hybrid composites prepared by sol-gel chemistry for use as dental restorative material or as a bone substitute for bone repair.

2. Background Information

Composites have been used as dental restorative materials since 1962. Bioceramics, such as hydroxyapatite are widely used as bone substitutes; however, they are brittle in nature. Composites described in the present invention combine the properties of polymers and that of the ceramics to provide the necessary strength and toughness. Though the formulation of the composite materials have changed in the last three decades, the underlying chemical process involved has not changed. An acrylate monomer is used as the source of resin, and silica is used as the filler material. Though these composites have superior aesthetic qualities, there are still problems with the mechanical properties such as toughness and wear resistance, problems with adhesion to the dentin of the tooth, and problems with shrinkage of the composite material once it has been placed in the tooth and is cured. These problems are more of an issue when the composite is used for posterior restoration.

Durability is a major problem with posterior composite restoration material. Life spans of large fillings are usually fewer than five years, which can be attributed to inadequate resistance to wear of composites under masticatory friction. The insufficient interaction between the reinforcing filler and the resin binder may be responsible for the lack of wear resistance of these composite materials. It has been demonstrated that an ultra fine compact filled composite has a Young's modulus higher than that of dentin. These composites also have good Vickers hardness and high compressive strength. This improvement and the mechanical properties of the ultra fine compact filled composite may be the result of better binding of filler particles with the resin.

Two of the other major problems associated with the present day dental restorative materials are lack of adhesion to the dentin and shrinkage of the resin during polymerization. The lack of adhesion results in micro leakage and formation of secondary cracks along the interface between the tooth and the restorative material. The shrinkage often occurs during the conversion of monomer to polymer and works against the formation of an adhesive bond between the resin and the dentin of the tooth. The new fourth generation composite materials use a hydrophilic primer which can penetrate into the dentin and produce enhanced adhesion of the composite material. Conditioning of the dentin of the tooth and the use of hydroxy ethyl methacrylate (HEMA) as a primer results in sheer bond strengths of 17–20 megaPascal (MPa). Even though the use of these materials and the conditioning of the dentin increases sheer bond strengths to acceptable levels, shrinkage is often a problem.

The shrinkage of commercially available filled composite resin ranges from 2.6%–7.1%. These shrinkage values differ as a result of their monomer composition, various degrees of polymerization, filler type, and filler concentration. Use of oxaspiro monomers have been considered as the precursor for the resin, but these monomers expand 3.5%–3.9% in volume under polymerization conditions, which is not acceptable.

The properties of a composite material are greatly influenced by the degree of mixing between the inorganic (filler) and the organic (resin) phases. In a molecularly tailored system, an organically modified ceramic precursor will result in the synchronous formation of inorganic (silica) and organic (resin) components. Such a composite could be obtained by using sol-gel chemistry. The mixing of the inorganic and organic matrix in these composites is at the molecular level, and the particles are often nanometer sized. As expected, these hybrid nano-composite materials have toughness three orders of magnitude higher than the ceramic alone. Depending upon the morphology, phase behavior and organic-inorganic ratios, these composite materials comprise a continuum ranging from glass reinforced organic polymer to polymer modified glass.

Composites obtained using conventional sol-gel chemistry suffer from shrinkage problems as a result of evaporation of excess solvents and water. Ellsworth et al. (*Chem. Mater.* 5:839–844 (1993)) disclose the synthesis of non-shrinking sol-gel composites with higher glass content using a modified esterification process for synthesizing poly-silicic acid esters with unsaturated alcohols. This method eliminates most of the shrinkage problems and long drying times required with conventional composites. However, the materials produced according to these methods are solids which are not particularly useful as dental restorative material, which requires a liquid to gum-like consistency. Additionally, these materials will have problems adhering to the dentin, and thus do not address the adhesion problems of composites.

Goodwin and Kenney in *Inorg. Chem.* 29:1216–1220 (1990) disclose a method of converting a silicate to an alkoxysiloxane using very simple alcohols, such as methanol, butanol, and ethanol in the presence of hydrochloric acid. No transformation of these compounds to composites is disclosed. Further, there is no suggestion to select and use alcohols containing particular functional groups responsible for imparting improved properties to ceramics produced from these compounds.

U.S. Pat. No. 4,381,918 to Ehrnford discloses a method of producing a dental restorative composite of organic resin and inorganic porous particles; however, the composite is not a "true" organic-inorganic composite. Sol-gel chemistry is not used to obtain this composite.

Other patents disclose processes of making organic-inorganic hybrid polymers, which are not disclosed to be useful as dental restorative materials. U.S. Pat. No. 5,064,877 to Nass et al. disclose a process of fixing inorganic species in an organic matrix. Monomeric compounds were reacted with complexing agents which have polymerizable functional groups. Hydrolysis and condensation took place prior to polymerization and polycondensation. The concentration of inorganic species in the matrix was small. U.S. Pat. No. 5,231,156 discloses the preparation of organic-inorganic hybrid polymers. A 5%–25% $R_xSi(OR')_{4-x}$ was mixed with 95%–75% of an organic monomer capable of a polymerization reaction with the R group.

A good dental material should possess a long lifetime, high toughness or durability, high abrasion resistance, superior adhesion to dentin, approximately 0% shrinkage/expansion, good esthetics, and comparable radiopacity to the enamel. At the present time, there are no dental restorative materials available which have all of these characteristics. Thus, there is a need in the dental field for a restorative material which has all of these characteristics.

The present invention provides a unique approach to producing a hybrid composite for dental restorative purposes or as a bone substitute. By selecting specific monomers (alcohols) having desired functional groups, alkoxides (single source precursors) containing these functional groups are obtained via esterification, and then transformed to hybrid composites having advantageous properties. These hybrid composites possess good adhesiveness attributable to the presence of the functional groups of the monomer which during the method are transferred by esterification to the single source precursor. Polynuclear alkoxides of silicon, aluminum, titanium, or zirconium can be obtained which will function as single source precursors for organic-inorganic hybrid composites of the present invention. These single source precursors can also contain mixtures of silicon, aluminum, titanium, and zirconium according to the present invention which are transformed to obtain mixed organic-inorganic hybrid composites. None of the prior art organic-inorganic composites possess the properties of low to no shrinkage, and good adhesion. As a result of being produced from a single source precursor, the components of the composite of the present invention are consistently mixed each time, whereas the prior art methods may result in the lack of uniform consistency due to mixing of components within a single preparation or among multiple preparations. None of the prior art discloses the use of a single source precursor containing the functional groups which result in enhanced properties of the resultant hybrid organic-inorganic composites.

The hybrid composites of the present invention consist of a net work of very fine, probably nanometer sized $SiO_2$ network, which is penetrated by acrylate based polymers. Because of the very small size of the $SiO_2$ particles, the composites of the present invention are transparent and translucent making them good candidates, particularly for dental restorative materials.

SUMMARY OF THE INVENTION

The present invention is based on the use of single source precursors to yield organic hybrid composites with none of the problems of the prior art hybrid composites.

The present invention further provides organic-inorganic hybrid composites possessing the desirable properties of superior adhesion to dentin, little or no shrinkage or expansion, and durability.

The present invention also provides a method of condensing and polymerizing (transforming) the single source precursor to produce an organic-inorganic hybrid composite with desirable properties.

The present invention provides a cost effective method of producing an organic-inorganic hybrid precursor which results in a hybrid composite material in which there is a consistent mixing of components each time because it is produced from a single source precursor rather from a mixture of components.

DETAILED DESCRIPTION OF THE PREFERRED EMBODIMENT

The single source precursors of the present invention are alkoxides of silicon, aluminum, titanium, and zirconium. Particularly alkoxides of silicon (siloxanes) obtained from oligo-/poly-silicic acid or cyclic silicic acid are preferred. In the preferred embodiment of the present invention, these siloxanes are alkoxides obtained by reacting suitable monomeric alcohols with these silicic acids via an esterification process. Oligo-/poly-silicic acid or cyclic silicic acids are selected which will provide high glass content resulting in high strength of the resulting hybrid composites.

The present invention discloses a single source precursor of an organic-inorganic hybrid composite comprising an alkoxide having the general formula $M_aO_b(OR)_c$, wherein M is selected from the group consisting of Si, Al, Ti, and Zr, when M=Si, then $a \geq 2$, b>1, and c>6; or when M=Al,Ti, or Zr, then a=2–7, b=1–6, and c=6–16; and wherein

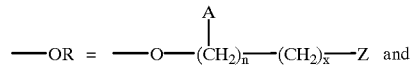

n is 0 or 1, x is 0 or 1 and A is selected from the group consisting of hydroxyl, carboxyl, sulfhydryl, amino, amide, and ester having the formula COOR', wherein R' is an alkyl or a substituted alkyl group, and Z is selected from the group consisting of alkene, vinyl, allyl and acrylic.

The selection of a suitable monomer (alcohol) is important because it should possess the functional groups that will make the alkoxide more easily polymerizable, and that will provide the characteristics of good adhesion, and reduced shrinkage to the ultimately produced hybrid composite. The suitable monomer should be unsaturated to impart the easy polymerizable function to the alkoxides, and it should also contain hydrophilic groups such as a hydroxyl, amino, thiol, carboxylic acid, amide, or ester groups which will provide the enhanced adhesive function to the ultimate hybrid composite.

The silicic esters are obtained by reacting the oligo-/poly-silicic acid or cyclic silicic acid with a monomer (alcohol) having the general formula for RO— as described above. The preferred method for obtaining a cyclic silicic ester is via a transesterification reaction with the alcohol of choice. These particular RO— groups can also be used to prepare the alkoxides of aluminum, titanium, and zirconium.

Specific examples of RO— groups are as follows:

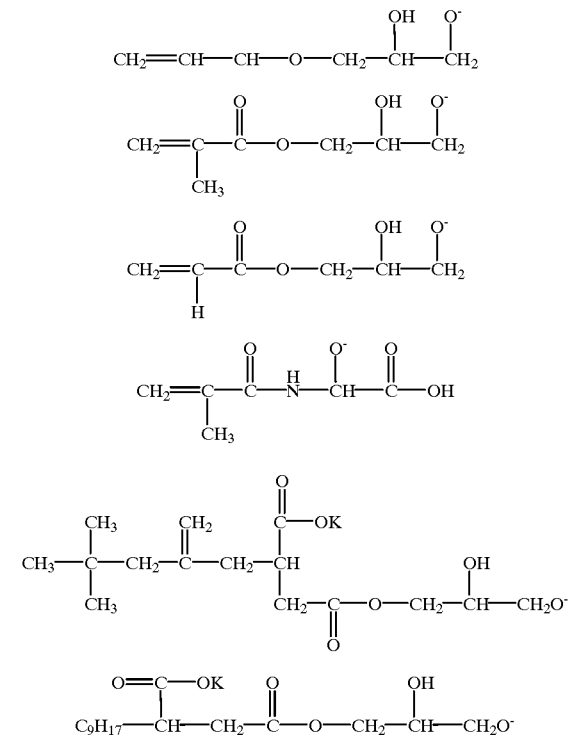

When M=Si and the alkoxide is derived from a poly-silicic acid, then preferably a=35–50, b=34–49, c=72–102, A=a hydroxyl or an amino group and Z=an acrylic group.

When M=Si and the alkoxide is derived from an oligo-silicic acid, then preferably a=10–20, b=9–19, c=22–42, A=a hydroxyl or an amino group and Z=an acrylic group.

When M=Si and the alkoxide is a cyclic silicic ester, then preferably a and b=3–6 and c=2a, Y=a hydroxyl or an amino group and Z=an acrylic group.

Preferably the RO— group is 2,3-dihydroxypropylmethacrylate when the alkoxide is derived from any of the oligo-, poly- or cyclic silicic acids.

As a result of the esterification reaction, most likely one of the hydroxyl groups on the silica is alkoxylated to an RO— group as defined above resulting in the siloxane. The reaction of all the available hydroxyl groups in the formation of the siloxane is preferred because it adds more stability against decomposition. The functional group A if unreacted during the esterification reaction will enhance the adhesion property of the ultimate composite material.

The alkoxide of oligo- or poly-silicic acid herein defined as Compound I has the following general formula:

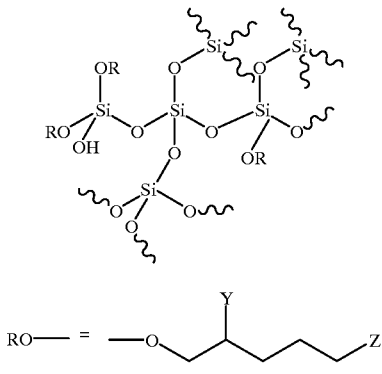

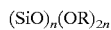

A=—OH, —COOH, —SH, —NH$_2$, —CONH$_2$, —COOR (R=alkyl or substituted akyl)

Z=Alkene, Vinyl, allyl and acrylic groups

The ester of cyclic silicic acid herein defined as Compound II is defined by the general formula:

(SiO)$_n$(OR)$_{2n}$

Examples of the specific RO— groups are the same as provided above for both Compounds I and II.

It is important that the single source precursor is a liquid ester with desirable viscosity which can be further used for synthesizing the hybrid composite of the present invention. The liquid silicic acid is more amenable for producing the hybrid composite of the present invention, however, a siloxane having at least a gel-like consistency can also be utilized in the present invention. A solid ester is not usable for further processing as a dental restorative material in the present invention.

The composites of the present invention are produced by reacting the alkoxide having an RO— group as defined above, with at least a curing agent and water in the presence of visible light, UV-light, or heat. The reaction can further include hardeners, such as hydroxyl ethyl methacrylate (HEMA) and Bisphenol A-bis(2-hydroxypropyl) methacrylate (Bis-GMA), or a promoting agent, such as 2-(dimethylamino)ethyl methacrylate (NDEM), or a combination of a hardener and promoting agent.

More specifically, after the single source precursors or siloxanes are produced as described above, they are then mixed with HEMA and Bis-GMA in the presence of a promoting agent and curing agent, water and light for a period of time sufficient for the formation of an organic-inorganic hybrid composite according to the present invention. Many different types of curing agents can be used in the method of the present invention. Any visible light curing agents, such as camphorquinone, 4-octyloxyphenylidoniumhexafluoroantimonate; and UV-light curing agents, such as arylsulphonium, and aryldiazonium salts, can be used in the present invention. Additionally, thermal initiated curing agents, such as peroxides, ketones and 2,2'-Azobisisobutyronitrile (AIBN) can be used. Any curing agent can be used in the present invention as long as it functions to cure the composite without any detrimental effect. Further any promoting agent can be used which will accelerate the transformation under the reaction conditions. Preferably amino promoting agents are used, such as, NDEM.

To obtain a hybrid composite with good mechanical properties, the hydrolysis and condensation of the siloxane should be concurrent with the polymerization. The rate of hydrolysis and condensation can be controlled by altering the pH and the quantity of water added. Visible light can be used to catalyze the polymerization, however, the hybrid can be cured under ultraviolet radiation in a range of wavelengths well known to persons skilled in the art. The composites of the present invention can also be cured by thermal curing agents. A visible light cure is preferred.

The present invention will be further understood from the following examples of preferred embodiments. These examples are not meant to limit the invention to these specific examples, but rather to show how the invention is performed in practice.

EXAMPLE 1

The synthesis of Compound I as described by the general formula above is as follows:

A solution of sodium metasilicate (4.25, 35 mmol) and 30 ml of water was added dropwise to 30 ml of 3.0N HCl at 0° C. The solution was stirred for approximately two hours. The solution of the silicic acid was extracted into tetrahydrofuran (THF) by adding 150 ml THF along with 40 g of NaCl. The THF layer was dried with anhydrous Na$_2$SO$_4$. To 100 ml of a THF solution of polysilicic acid, 50 ml of 3-allyoxy-1,2-propanediol was added. This solution was heated and the THF/H$_2$O azeotrope removed until 75 ml was collected. At this point, dry THF was added continuously and distilled, until 500 ml had been collected. The solution was vacuum distilled (0.02 mm of Hg) to removed 30 ml of unreacted diol to produced Compound I.

Compound I was condensed and polymerized to form Composite I as follows: Sixty percent (60%) by weight of Compound I was reacted with a mixture of 40% by weight of a approximately 50:50 mixture of HEMA and Bis-GMA in the presence of 2-(dimethylamino)ethyl methacrylate (NDEM) (5 drops), camphoroquinone (CQ) (10 mg), water (1 drop) and visible light for approximately 5–6 hours. This reaction resulted in the formation of Composite I, a condensation and polymerization product of Compound I, as described above.

Composite I can be prepared from the following range of compounds: Compound I—56–96%, HEMA—0–20%, Bis-GMA—0–20%, CQ—0.2–0.7%, NDEM—0.5–1.5%, and water—1.5–4%.

EXAMPLE 2

Ca$_8$(SiO$_3$)$_4$Cl$_8$ was used as the source of cyclic silicic ester and was prepared by heat treating a mixture of Wallostonite (CaSiO$_3$) and CaCl$_2$.2H$_2$O at 775° C. for 16.5 hours. Characterization of Ca$_8$(SiO$_3$)$_4$Cl$_8$ was performed by different techniques including x-ray diffraction (XRD). The d values observed for different peaks were identical to the reported values. Ca$_8$(SiO$_3$)$_4$Cl$_8$ (10 g) was added to a solution containing 180 ml of toluene and 160 ml of anhydrous ethanol. To this suspension, 11 ml of 9M anhydrous, ethanolic HCl was added dropwise over a period of 15 minutes. This solution was distilled until 270 ml of distillate was collected. The remaining suspension was filtered and the filtrate collected. The solid material was washed with 35 ml of dry hexane and the washing was collected. The combined filtrates were concentrated to an oil under vacuum (<0.1 mm of Hg.) This material was analyzed by $^1$H and $^{13}$C NMR and characterized as (SiO)$_4$(OEt)$_8$, and determined to be of sufficient purity for further studies. To a solution of (SiO)$_4$(OEt)$_8$ (3 g), 2,3 dihyroxypropyl methacrylate (30 ml) and a catalytic amount of HCl in ethanol were added. This solution was heated to 50° C. and was periodically evacuated to remove any ethanol which was released during the reaction. After 1 hour of heat treatment, the solution was cooled to room temperature resulting in a light yellow oil.

The formation of Compound II is as follows:

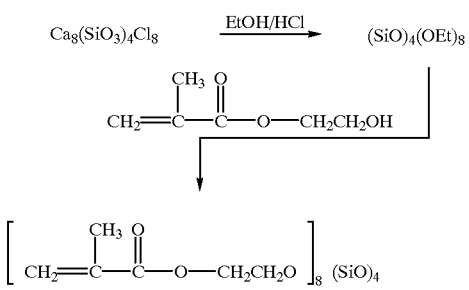

Sixty percent (60%) by weight of Compound II was reacted with 40% by weight of a mixture of HEMA and Bis-GMA in the presence of 2-(dimethylamino) ethyl methacrylate (NDEM) (5 drops), camphorquinone (CQ) (10 mg), water (1 drop) and visible light for approximately 5–6 hours. This reaction resulted in the formation of Composite II, a condensation and polymerization product of Compound II, as described above.

EXAMPLE 3

Composite I (polysilicic alkoxide) was tested using a toothbrush three-body abrasion test. Prior to running the abrasion test, the specimen was ground from its original thicknesses of 4–5 mm to a 2 mm thickness and then finished with a series of abrasive cloths beginning with 80 grit and ending with 400 grit. The final specimen was soaked in distilled water for 1 hr. dried with tissue paper, and then air dried overnight.

The toothbrush abrasion test was run for a total of 32 hours. The specimen of 2 mm thickness was placed in an abrasion test machine consisting of eight test stations, with a toothbrush mounted at each station. For this experiment three stations were utilized, each with an Oral-B P40 soft bristle toothbrush that contained 47 tufts. The specimen was covered with 96 grams of toothpaste (CREST with Fluoristat®) and subjected to 10,000 stroke/hr for two hours. The specimen was removed after each two-hour run, rinsed thoroughly with distilled water, air dried for two hours and reweighed. This was repeated three times for a total brushing time of eight hours.

The resulting data are given in Table 1 below.

TABLE 1

Results of toothbrush three-body abrasion study

| Brushing Time (hrs) | Specimen Polysilicic | |
|---|---|---|
| | wt (g)* | wt loss (g) |
| 0 | 2.3819 | 0.0000 |
| 2 | 2.3804 | 0.0015 |
| 4 | 2.3629 | 0.0190 |
| 6 | 2.3533 | 0.0286 |
| 8 | 2.3442 | 0.0377 |

*wt = Weight of specimen together with its mounting base

The abrasive loss and overall rate of change for each specimen are show in Table 2:

TABLE 2

Weight loss during three-body abrasion with toothbrush and dentifrice

| | Abrasion wt. loss (mg) | | | | Rate (8 hr avg) |
|---|---|---|---|---|---|
| Specimen | 2 hr | 4 hr | 6 hr | 8 hr | mg/hr |
| Polysilicic | 0.15 | 1.90 | 2.86 | 3.77 | 4.7 |

These results show that there is less than 5 mg of weight loss per hour which is comparable to known dental composite materials.

The present invention has been described in detail; however, it is to be understood that the invention as defined by the appended claims is not to be limited by particular details set forth in the above description as many apparent variations thereof are possible without departing from the spirit or scope thereof.

I claim:

1. A single source liquid precursor to an organic-inorganic hybrid composite comprising:

an alkoxide having the general formula M$_a$O$_b$(OR)$_c$, wherein

M is selected from the group consisting of Si, Ti, and Zr, when M=Si, then a≧2, b>1, and c>6; or when M=Al,Ti, or Zr, then a=2–7, b=1–6, and c=6–16; and wherein

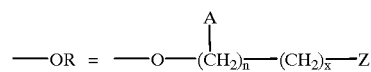

n and x are each 0 or 1, and

A is selected from the group consisting of hydroxyl, carboxyl, sulfhydryl, amino, amide, and ester having the formula COOR', wherein R' is an alkyl or a substituted alkyl group, and Z is selected from the group consisting of alkene, vinyl, allyl and acrylic.

2. The single source precursor of claim 1, wherein M=Si and the alkoxide is condensed from a poly-silicic acid.

3. The single source precursor of claim 2, wherein a=35–50, b=34–49, c=72–102, A=a hydroxyl or an amino group and Z=an acrylic group.

4. The single source precursor of claim 3, wherein RO—= 2,3-dihydroxypropylmethacrylate.

5. The single source precursor of claim 1, wherein M=Si and the alkoxide is condensed from an oligo-silicic acid.

6. The single source precursor of claim 5, wherein a=10–20, b=9–19, c=22–42, A=a hydroxyl or an amino group and Z=an acrylic group.

7. The single source precursor of claim 6, wherein RO—=2,3-dihydroxypropylmethacrylate.

8. The single source precursor of claim 1, wherein M=Si and the alkoxide is a cyclic silicic ester, then a and b=3–6 and c=2a, A=a hydroxyl or an amino group and Z=an acrylic group.

9. The single source precursor of claim 8, wherein RO—=2,3-dihydroxypropylmethacrylate.

10. An organic-inorganic hybrid composite comprising the reaction product of:
   (a) an alkoxide having the general formula $M_aO_b(OR)_c$,
      wherein M is selected from the group consisting of Si, Al, Ti, and Zr,
      when M=Si, then $a \geq 2$, b>1, and c>6; or
      when M=Al,Ti, or Zr, then a=2–7, b=1–6, and c=6–16;
      and wherein

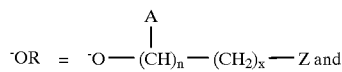

n and x are each 0 or 1, and
   A is selected from the group consisting of hydroxyl, carboxyl, sulfhydryl, amino, amide, and ester having the formula —COOR', wherein R' is an alkyl or a substituted alkyl group, and
   Z is selected from the group consisting of alkene, vinyl, allyl and acrylic;
   (b) a curing agent; and
   (c) water.

11. The organic-inorganic hybrid composite of claim 10, wherein M=Si and the alkoxide is condensed from a poly-silicic acid.

12. The organic-inorganic hybrid composite of claim 11, wherein a=35–50, b=34–49, c=72–102, A=a hydroxyl or an amino group and Z=an acrylic group.

13. The organic-inorganic hybrid composite of claim 12, wherein RO—=2,3-dihydroxypropylmethacrylate.

14. The organic-inorganic hybrid composite of claim 10, wherein M=Si and the alkoxide is derived from an oligo-silicic acid.

15. The organic-inorganic hybrid composite of claim 14, wherein a=10–20, b=9–19, c=22–42, A=a hydroxyl or an amino group and Z=an acrylic group.

16. The organic-inorganic hybrid composite of claim 15, wherein RO—=2,3-dihydroxypropylmethacrylate.

17. The organic-inorganic hybrid composite of claim 10, wherein M=Si and the alkoxide is a cyclic silicic ester, then a and b=3–6 and c=2a, A=a hydroxyl group and Z=an acrylic group.

18. The organic-inorganic hybrid composite of claim 17, wherein RO—=2,3-dihydroxypropylmethacrylate.

19. The organic-inorganic hybrid composite of claim 10, wherein said curing agent is selected from the group consisting of visible light curing agents, UV-light curing agents, and thermal initiated curing agents.

20. The organic-inorganic hybrid composite of claim 10, further comprising a hardener.

21. The organic-inorganic hybrid composite of claim 20, wherein said hardner is selected from the group consisting of hydroxylethyl methacrylate, Bisphenol A-bis(2-hydroxypropyl) methacrylate and a combination thereof.

22. The organic-inorganic hybrid composite of claim 10, further comprising a promoting agent.

23. The organic-inorganic hybrid composite of claim 20, further comprising a promoting agent.

24. A method of making an organic-inorganic hybrid composite comprising:
   a. obtaining an alkoxide having the general formula $M_aO_b(OR)_c$, wherein M is selected from the group consisting of Si, Al, Ti, and Zr,
      when M=Si, then $a \geq 2$, b>1, and c>6; or
      when M=Al,Ti, or Zr, then a=2–7, b=1–6, and c=6–16;
      and wherein

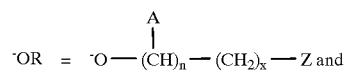

n and x are each 0 or 1, and
   A is selected from the group consisting of hydroxyl, carboxyl, sulfhydryl, amino, amide, and ester having the formula —COOR', wherein R' is an alkyl or a substituted alkyl group, and
   Z is selected from the group consisting of alkene, vinyl, allyl and acrylic; and
   b. concurrently and polymerizing said alkoxide in the presence of at least a curing agent and water to form an organic-inorganic hybrid composite.

25. The method of claim 24, wherein said curing agent is selected from the group consisting of visible light curing agents, UV-light curing agents, and thermal initiated curing agents.

26. The method of claim 24, wherein said condensation and polymerization further occurs in the presence of a hardener.

27. The method of claim 26, wherein said hardener is selected from the group consisting of hydroxylethyl methacrylate, Bisphenol A-bis(2-hydroxypropyl) methacrylate and a combination thereof.

28. The method of claim 24, wherein said condensation and polymerization further occurs in the presence of a promoting agent.

29. The method of claim 26, wherein said condensation and polymerization further occurs in the presence of a promoting agent.

* * * * *